US00PP12909P2

(12) United States Plant Patent
Skwiot

(10) Patent No.: US PP12,909 P2
(45) Date of Patent: Sep. 3, 2002

(54) *PENNISETUM ORIENTALE* 'KARLEY ROSE'

(75) Inventor: David George Skwiot, Kensington, CT (US)

(73) Assignee: Sunny Borden Nurseries Inc., Kensington, CT (US)

( * ) Notice: Subject to any disclaimer, the term of this patent is extended or adjusted under 35 U.S.C. 154(b) by 0 days.

(21) Appl. No.: 09/470,740

(22) Filed: Dec. 23, 1999

(51) Int. Cl.[7] ..... A01H 5/00
(52) U.S. Cl. ..... Plt./384
(58) Field of Search ..... Plt./384

(56) References Cited

PUBLICATIONS

UPOV–ROM GTITM Computer Database, GTI JOUVE retrieval software, citation for 'Karley's Rose', Aug. 2000.*

* cited by examiner

*Primary Examiner*—Bruce R. Campell
*Assistant Examiner*—Annette Para

(57) ABSTRACT

*Pennisetum orientale* 'Karley Rose' is a new and distinct cultivar of Oriental Fountain Grass with deep green foliage, dark purple flowers effective for 16 to 18 weeks, and freeze hardy at least to temperatures of −15° F. (−26° C.).

4 Drawing Sheets

BRIEF SUMMARY OF THE PLANT

The present invention, *Pennisetum orientale* 'Karley Rose', is a new and distinct form of the ornamental Oriental Fountain Grass, and hereinafter is referred to by the cultivar name, 'Karley Rose', or as "the plant".

The plant was discovered in July of 1994 by David G. Skwiot at a nursery in Kensington, Conn. It was one plant selected from a large number of other seedling plants grown under cultivation in containers and then separated for further evaluation. Due to the unique and marketable differences in the plant from other Oriental grasses, Mr. Skwiot asexually propagated the plant by division at the same nursery in Kensington, Conn. for further evaluation and to build up stock. The resulting plants are identical to the original parent plant.

BACKGROUND OF THE PLANT

The Oriental Fountain Grass, *Pennisetum orientale*, is native to the area from central Asia and northern and western India to the Caucasus Mountains. Its foliage at maturity measures eighteen to twenty-four-inches (45 to 60 cm) long and ⅛ to ¼ inch (0.3 to 0.6 cm) wide. Plants form clumps or mounds that are 24 to 36 inches (60 to 90 cm) tall when in flower or fruit. Flowers are formed in terminal spikes that may be one to one and one half inches (2.5 to 3.8 cm) wide and six to eight inches (15 to 20 cm) long. The spike is an erect stem with terminal bristled spikelets with the bristles longer than the spikelets. The usual 65 to 70 florets altogether produce an overall cream to creamy pink color, usually about 156 A on The Royal Horticultural Society Colour Chart, effective from June into September in Connecticut. The height during flowering may be between 16 and 32 inches (40 to 80 cm). Foliage is normally about a 137 C (on the R.H.S. Colour Chart), and is about ¼ inch (0.6 cm) wide and 18 to 24 inches (45 to 60 cm) long.

In July of 1994 David G. Skwiot was walking through some fields of seed propagated ornamental Oriental Fountain Grass at a nursery in Kensington, Conn. He noticed a single plant that stood out because of its unique characteristics. The plant looked to be more erect, taller and have darker green foliage compared to all other seedlings viewed and previously grown by the inventor. Upon further evaluation the plant was noted as having a darker, wider, longer and fuller inflorescence than the other seedlings as well. The plant was then evaluated further over the next several years.

BRIEF DESCRIPTION OF THE DRAWINGS

The accompanying color photographs illustrate the unique characteristics of the plant, and depict the true colors to the greatest degree possible with color reproductions.

DETAILED DESCRIPTION OF THE PLANT

Figure 1:
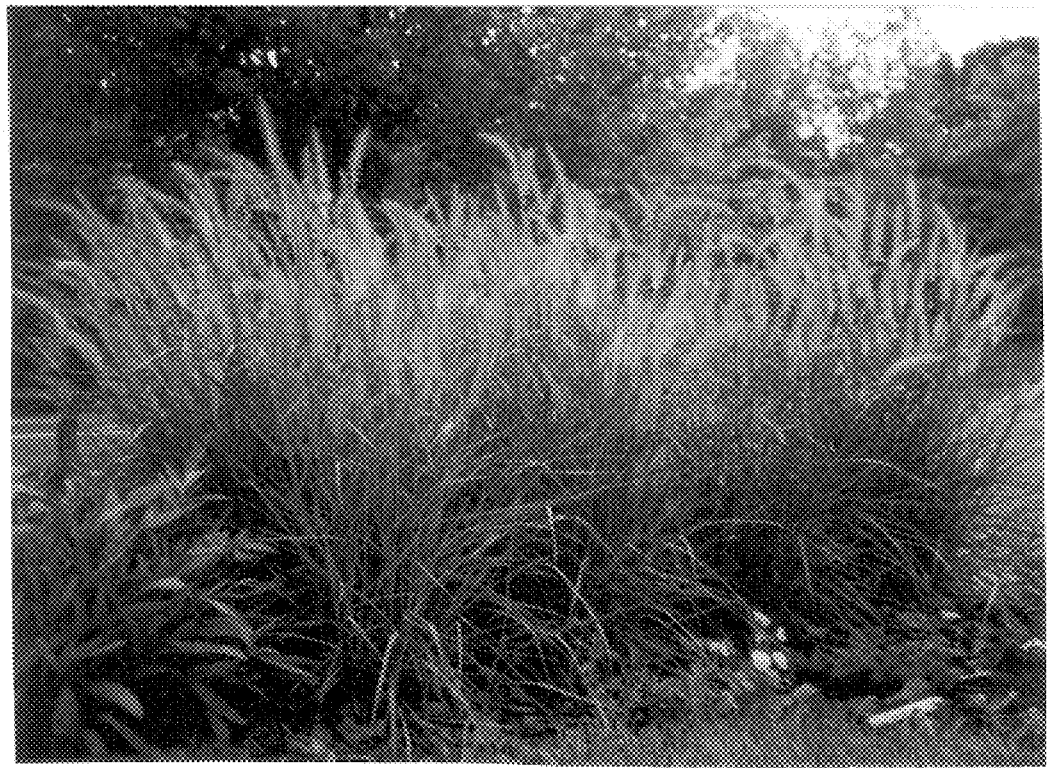
FIG. 1 shows the plant in flower in a garden situation.
Figure 2:
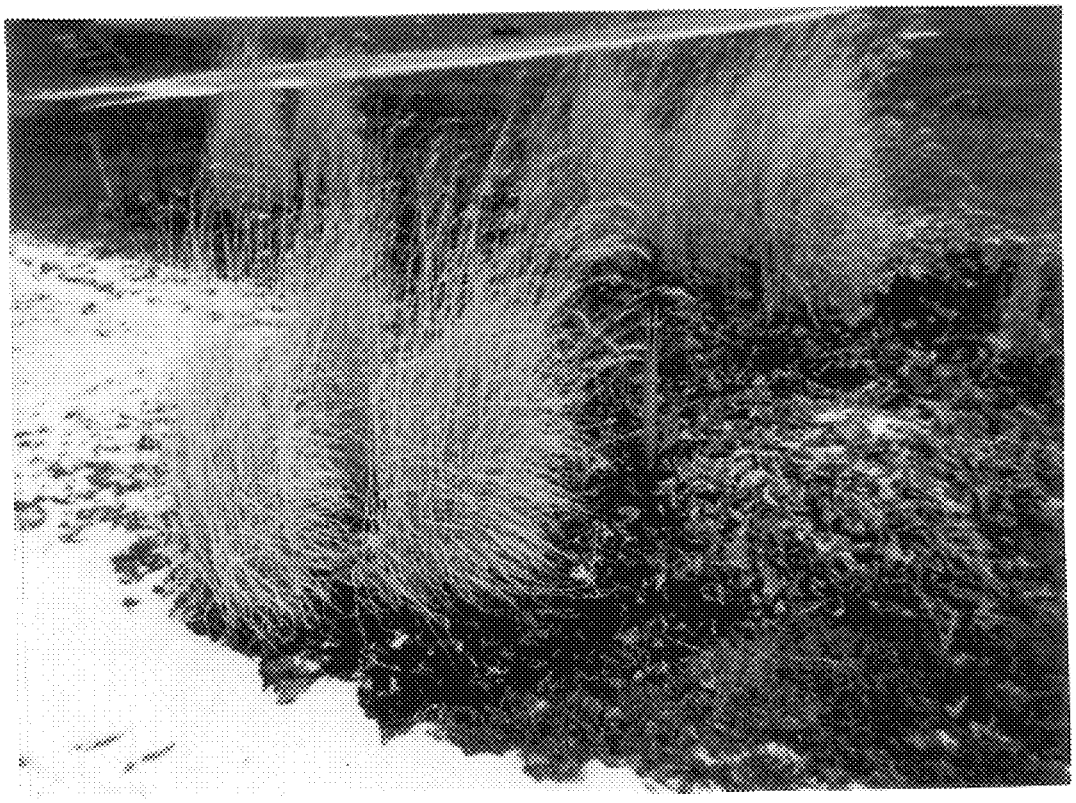
FIG. 2 shows the plant in its winter habit with normal sun bleached foliage and flowers.
Figure 3:
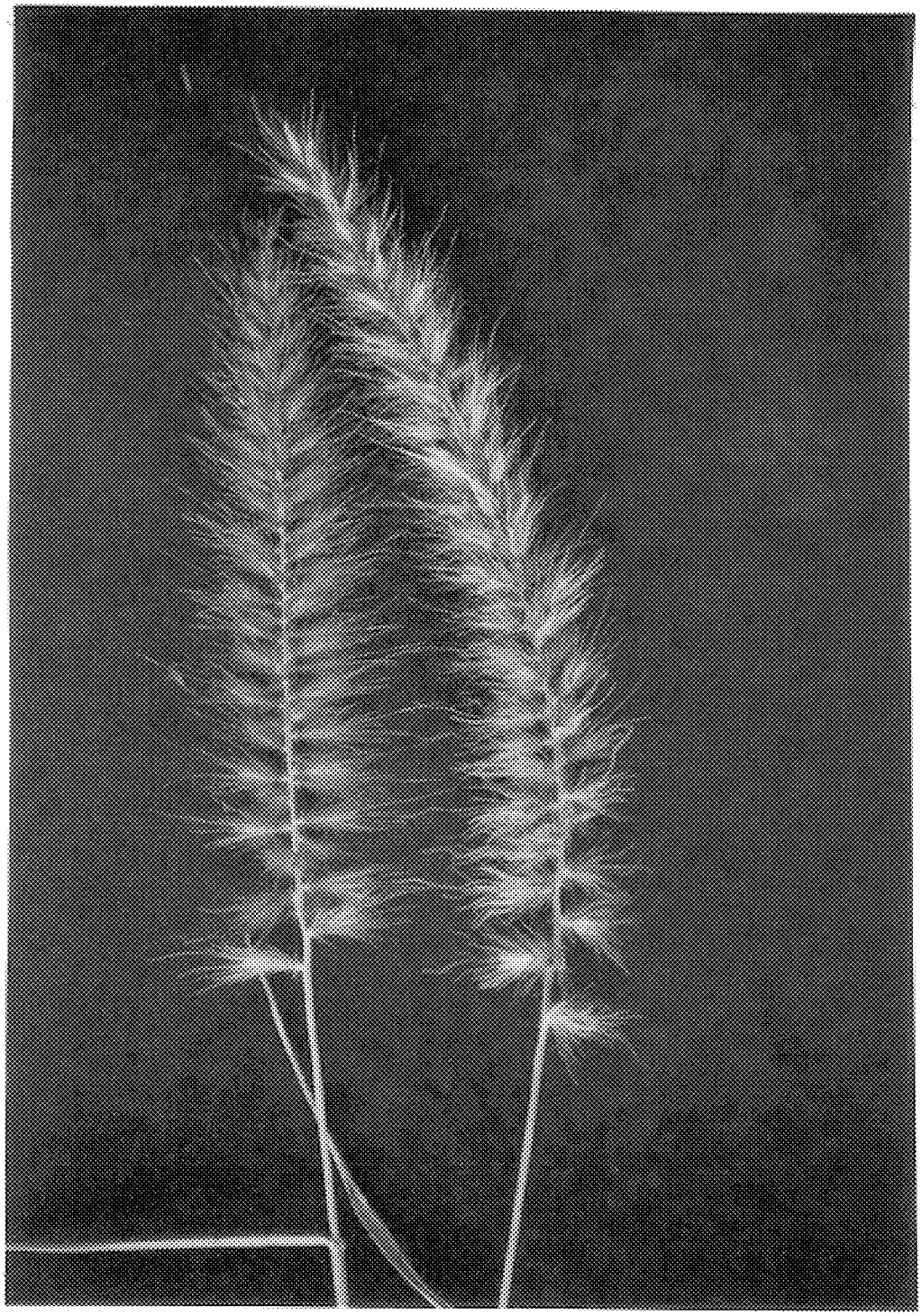
FIG. 3 demonstrates both young (left) and old (right) flowers.
Figure 4:
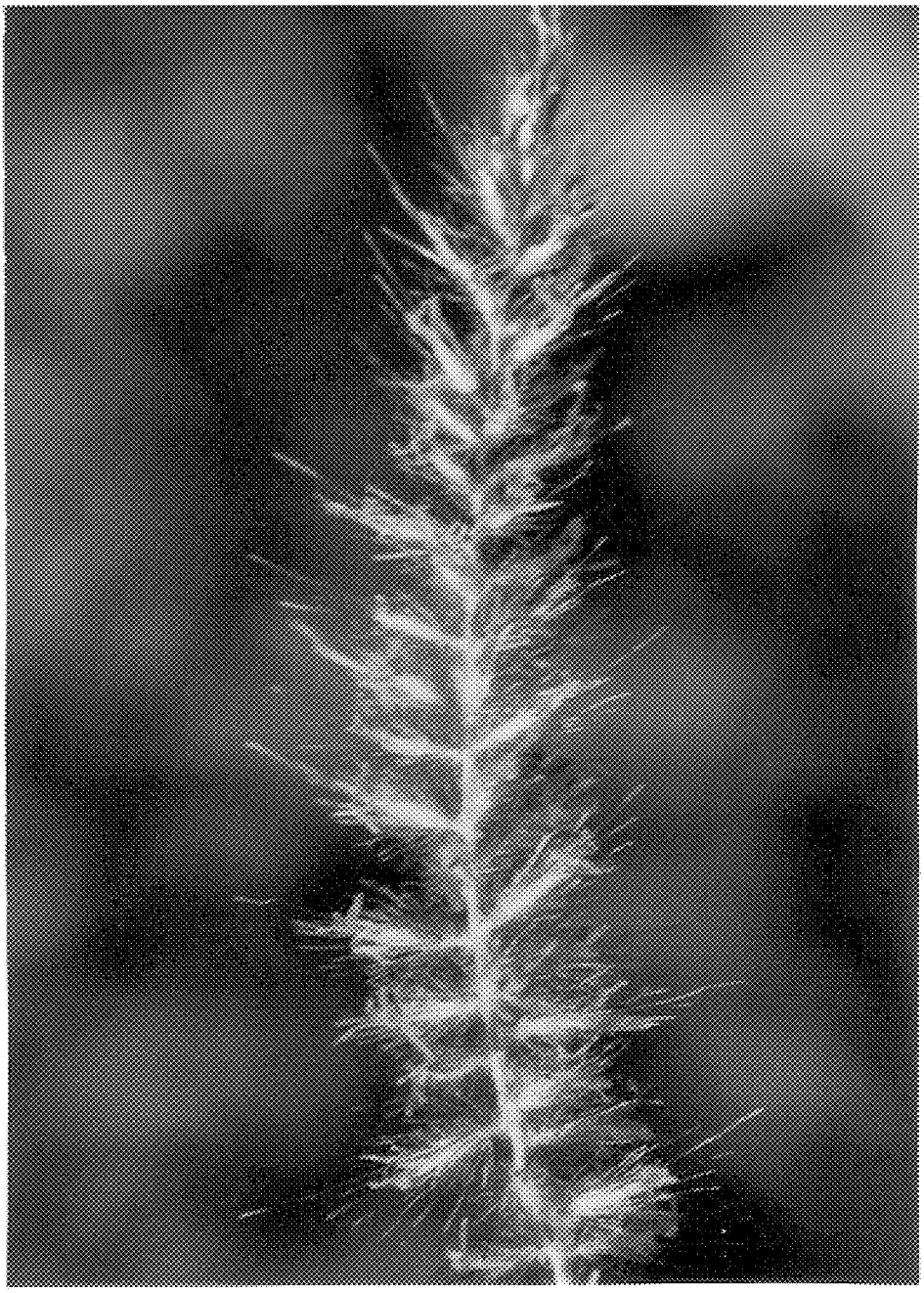
FIG. 4 shows a close-up view of the flower spikes.

*Pennisetum orientale* 'Karley Rose' is a seedling selection of Oriental Fountain Grass discovered and evaluated at a nursery in Kensington, Conn. The plant is a unique individual that has a more colorful and extended ornamental bloom period. The flower spike on 'Karley Rose' starts much darker lavender than other plants of the species known to the inventor, and its color continually deepens as it gets near peak period. The plant consistently shows excellent improved winter hardiness beyond the normal species. It has survived temperatures of at lease −15° Fahrenheit.

All the following color descriptions are based on the color terminology in accordance with The Royal Horticultural Colour Chart and are labeled with R.H.S. and the corresponding identification numbers. The plant herein described is a three year old specimen grown in an irrigated sunny garden in Kensington, Conn.

*Pennisetum oriental*'Karley Rose' is a unique herbaceous ornamental grass. Individual leave blades are ¼ to ⅜ inch (0.6 to 10 cm) wide and 24 to 30 inches (60 to 75 cm) long. Culms are erect or decumbent becoming erect to a height of 36 to 42 inches (or 91 to 106 cm). Leaves are arching in the flat section, and leaf sheaths rounded on back. The culms are pubescent, and leaves slightly pubescent underneath. Leaves are a green group R.H.S. 137 B. The tight clumps are 36 to 42 inches (91 to 106 cm) high.

The inflorescences on the plant are eight to 10 inches (20 to 25 cm) long and ¾ inch to 1¼ inch (2.0 to 3.0 cm) wide on stems 42 to 48 inches (110 to 125 cm) tall. The inflorescence is a spike-like panicle made up of over one hundred individual florets with up to 25 dark bristles each. The bristles are near R.H.S. 187 A, and vary in length from 1/16 inch to ⅞ inch (3 mm to 22 mm) long, much longer than the spikes, effective from late May through the end of October in Connecticut, about one and a half months longer than the normal *P. oriental*. The two sets of glume are both about ¼ inch (6 mm) long and R.H.S. 161 D in the middle and R.H.S. 164 at both ends. The inflorescence color begins a light lavender, about a R.H.S. 59 C, and in peak flowering darkens to a purple R.H.S. 59 A, and after flowering dries to a beige, about R.H.S. 199 B. The winter color lightens to R.H.S. 161 D.

Plant sizes and colors may vary depending on growing conditions, amount of sunlight, fertility, and maturity of the plant.

The rhizome is short, slowly creeping to 5/16 inch (8 mm) in diameter. The root is stiff; fibrous and freely branching. The plant is fertile and seed and sexual organs are identical to the species.

There are several other differences between *Pennisetum orientale* 'Karley Rose' and the normal species. The plant, 'Karley Rose' has a very deep purple flower in its prime and flowers for five to six weeks longer, compared to the most of the other species. In Connecticut, the species flowers from late June into September, whereas 'Karley Rose', because of its tendency to rebloom, has flowers effective from late May until the end of Octover. The panicle of the plant is also fuller, longer and wider than the species. The foliage color of 'Karley Rose' is deeper green, a R.H.S. 137 B compared to the R.H.S. 137 C observed in the species. The last difference is that the plant is much hardier than the typical species. The species has been found to be frost tender at temperatures below 0° F. (−17° C.). However, *Pennisetum orientale* 'Karley Rose' has survived temperatures down to at least −15° F. (−26° C.). The plant is not susceptible to any major pests or diseases and is resistant to drought and heat of temperature of 100° F. or more.

I claim:

1. The new and distinct variety of Oriental Fountain Grass, *Pennisetum orientale* plant, 'Karley Rose', essentially as herein described and illustrated, with deep green foliage, dark purple flowers effective for 16 to 18 weeks, and hardy to at least temperatures down to −15° F. (−26° C.).

* * * * *